United States Patent [19]

Hintersehr

[11] Patent Number: 5,702,650

[45] Date of Patent: Dec. 30, 1997

[54] PROCESS FOR PRODUCING DENTAL PROSTHESES

[76] Inventor: Josef Hintersehr, Gross-Gerauerstr. 49, D-64347, Gries/heim, Germany

[21] Appl. No.: 610,306

[22] Filed: Mar. 4, 1996

Related U.S. Application Data

[63] Continuation-in-part of Ser. No. 264,630, Jun. 23, 1994, abandoned.

[30] Foreign Application Priority Data

Jun. 24, 1993 [CH] Switzerland .................. 01894/93

[51] Int. Cl.[6] .................. A61C 13/00; A61C 13/08
[52] U.S. Cl. .................. 264/16; 264/19; 264/40.1; 264/648; 264/651
[58] Field of Search .................. 264/16, 19, 67, 264/60, 40.1, 651, 648

[56] References Cited

U.S. PATENT DOCUMENTS

| | | | |
|---|---|---|---|
| 5,121,660 | 6/1992 | Kramer | 76/104.1 |
| 5,192,472 | 3/1993 | Andersson | 264/40.1 |

*Primary Examiner*—Christopher A. Fiorilla
*Attorney, Agent, or Firm*—Bachman & LaPointe, P.C.

[57] ABSTRACT

A process for producing ceramic dental prostheses, with which ceramic dental prostheses may be produced in the same diversity of shapes and with the same accuracy as metal dental prostheses. The process includes shaping an unfinished piece made out of 92.1 to 93.5 wt. % zirconium oxide, 4.5 to 5.5 wt. % yttrium oxide, 1.8 to 2.2 wt. % hafnium oxide, and reworking the piece to form a dental prosthesis by means of a rotating tool made of metal-bonded diamond grains.

7 Claims, No Drawings

PROCESS FOR PRODUCING DENTAL PROSTHESES

CROSS-REFERENCE TO RELATED APPLICATION

This application is a Continuation-In-Part of U.S. patent application Ser. No. 08/264,630, filed Jun. 23, 1994 now abandoned.

BACKGROUND OF THE INVENTION

The invention concerns a process for producing dental prostheses out of ceramic materials.

Metal and ceramic materials for producing prostheses (endoprostheses, exoprostheses) are known. Metal is used predominantly in the case of producing high-precision prostheses of complicated configuration, which is very particularly true for dental prosthetics. Titanium alloys (TIAL6N, TIAL6Nb), which, in contrast to other metals known in prosthetics, are resistant against the pH variations of mouth fluid which exist in the mouth area, have become prevalent in dental prosthetics. Titanium and its alloys may be processed very well with known metal-working procedures, so that dental prostheses, the term dental prostheses here is to be understood as meaning crowns, bridges, inlays, dentures, and implants, of very complicated configuration may be made with very great precision with the known processing procedures starting from this metal. However, the disadvantage of dental prostheses made out of titanium and titanium alloys lies in the fact that all parts cannot be made sufficiently strong. A further disadvantage is the fact that a metal prosthesis has to be provided with a coating or a layer for covering the metal color in order to give the prosthesis the same or similar color as the rest of the set of teeth for aesthetic reasons.

Up to now ceramic materials have not been used extensively in dental prosthetics, although ceramic prostheses should be characterized by high strengths. Also, it would be possible to eliminate the color matching which goes along with metal prostheses. Two essential reasons are responsible for this, i.e., the dense vitrification or infiltration required, with the resulting difficulties in working the material and the requirement for biocompatibility, that is, body compatibility of the ceramic. Dental prostheses have to be made accurate with respect to shape and mass so that they can fulfill their specified purpose. It would not be possible to make ceramic prostheses accurate with respect to shape and mass if they were porous, i.e., comparatively soft. In this condition, tolerances comparable to those of metal prostheses may be obtained. However, porous ceramic dental prostheses are unusable. In every case, they have to be densely vitrified or infiltrated so that they assume the properties with which they are technically and aesthetically superior to metal dental prostheses. However, dense vitrification and infiltration change the shape and mass accuracies obtained in the porous condition, so that a densely vitrified ceramic dental prosthesis would have to be refinished in a second manufacturing step. However, densely vitrified or infiltrated change the shape and mass accuracies obtained in the porous condition, so that a densely vitrified ceramic dental prosthesis would have to be refinished in a second manufacturing step. However, densely vitrified or infiltrated ceramic parts assume such hardnesses and strengths that a reworking of objectively complex-shaped, small and very small parts of very high precision, such as dental prostheses, is very difficult, if not excluded. The material requirements to be imposed on ceramics as prosthesis materials are added to these limitations. It is required that prosthesis ceramics be bioinert, i.e., they must be resistant against body fluids. In order to avoid the absorption of body fluids they must be vitrifiable or infiltratable without significant shrinkage and warping. Corrosion resistance also is required so that a dental prosthesis is resistant against chemical attack and wear. Ceramic materials for the purpose of the invention have to fulfill the above-mentioned requirements in their entirety. Non-fulfillment of one leaves a ceramic material out of consideration for dental prostheses.

Two ceramic materials have qualified themselves for greater load-carrying endo- and exoprosthesis, e.g. joint balls, namely aluminum oxide ($Al_2O_3$) and an $Al_2O_3$ portion of 99.85%, balance other components and zirconium oxide ($ZrO_2$) in a predominantly tetragonal structure, stabilized by magnesium oxide ($MgO_2$) or by an oxide of the rare earth elements, preferably yttrium oxide ($Y_2O_3$) or cerium oxide ($CeO_2$). In the opinion of the scientific world they are not suitable for small or very small prostheses of complicated configuration requiring very high mass and shape accuracy, such as dental prostheses, because of the dense vitrification with the resulting hardness which resists finishing.

Proceeding from this, the task of the invention is to create a process for producing ceramic dental prostheses with which ceramic prostheses of the same accuracy of shape and mass as metal prostheses may be produced, thus the process is to be directed toward ceramics which lend the dental prostheses high strength, chemical resistance, and biocompatibility, and give prostheses a color appearance which corresponds to the other parts of the set of teeth without, or with only slight, finishing.

SUMMARY OF THE INVENTION

Surprisingly it has now been found that it is possible to make densely vitrified ceramic dental prostheses, i.e., in accordance with the invention dental prostheses consisting of zirconium oxide, of the same accuracy of shape and mass as metal dental prostheses. Because of the great hardness of densely vitrified zirconium oxide it was not to be expected that the required accuracies of shape and mass would be obtained with the process parameters in accordance with the invention. In accordance with the invention, the zirconium oxide is bioinert, biocompatible, and fulfills all further requirements imposed on ceramic prosthetic materials, so that with the invention the introduction of the ceramic into small and very small part prosthetics, i.e. dental prosthetics, is obtained with the advantages resulting therefrom.

The present invention comprises a process for producing ceramic dental prosthesis, which comprises: (a) shaping an unfinished piece made out of 92.1 to 93.5 wt. % zirconium oxide ($ZrO_2$), 4.5 to 5.5 wt. % yttrium oxide ($Y_2O_3$), 1.8 to 2.2. wt. % hafnium oxide ($HfO_2$), up to 0.2 wt. % of any other oxides; and (b) reworking the unfinished piece to form a dental prosthesis by means of a rotating tool having a circumference and being made of metal-bonded diamond grains with speeds of revolution for the tool of 10,000 to 50,000 revolutions per minute, with a first movement of the tool towards the piece of 0.1 to 0.5 millimeters per minute, and a second movement of the tool perpendicular to the first movement of 0.3 to 3.0 centimeters per second, and rotational speed along the circumference of the tool of 0.5 to 9.0 m/sec.

DETAILED DESCRIPTION OF PREFERRED EMBODIMENTS

In accordance with the invention, the maker of the prosthesis has the ability to produce a dental prosthesis from a densely vitrified or infiltrated semifinished piece, for example a disk of zirconium oxide, in that the prosthesis is made out of this semifinished piece by machine according to a pattern. Also, in accordance with the invention, it is possible to start first from a porous unfinished piece, rework this into a prosthesis making allowances in dimensioning, and then to finish to the final shape and mass by means of the process invented.

Within the framework of the invention also a mold and slip casting may be used to make an unfinished dental prosthesis, to dry it, to bake it, to redensity it hot-isostatically, and then to retreat it by oxidizing it; subsequently the unfinished piece corresponding to a prosthesis may be finished in accordance with the invention.

The invention will be explained in greater detail below by means of an example from dental prosthetics. The example described in connection with a crown also may be used for bridges, inlays, dentures, and implants, keeping the tools and processing parameters in accordance with the invention, it being possible that the preparation of a prosthesis may experience changes in the individual case.

EXAMPLE

The production of a disk (approximate mass given) consisting of yttrium-stabilized, predominantly tetragonally shaped zirconium oxide of the composition $ZrO_2$ 92.1 wt. % to 93.5 wt. %, $Y_2O_3$ 4.5 wt. % to 5.5 wt. %; $HfO_2$ 1.8 wt. % to 2.2 wt. %, impurities at most 0.2%, dense vitrification of the disk, digital acquisition and calculation of a full-scale crown model prepared by the dentist with internal and external contour, inputting the acquisition and calculation data into a data processing control unit for controlling a processing device movable in three coordinates, clamping the disk in a holder and reworking the unfinished piece to form a dental prosthesis by means of a rotating tool, with adjusting the speed of revolution of the tool (16,000 rpm) of a metal-bonded diamond drill as a grinder, the infeed or first movement of the tool towards the piece being 0.1 to 0.5 mm per minute, the second movement of the tool perpendicular to the first movement or advance being 0.3 to 3.0 centimeters per second, and the rotational speed along the circumference of the tool being 0.5 to 9.0 meters per second, roughing out the inner contour of the crown starting from a first side of the disk, roughening out the outer contour of the crown starting from the side opposite the first side of the disk, cutting out the preparation line and crown out of the disk separately. Then the crown is to be cleaned.

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

What is claimed is:

1. A process for producing a ceramic dental prosthesis, which comprises:
   (a) shaping an unfinished piece made out of 92.1 to 93.5 wt. % zirconium oxide ($ZrO_2$), 4.5 to 5.5 wt. % yttrium oxide ($Y_2O_3$), 1.8 to 2.2. wt. % hafnium oxide ($HfO_2$), and up to 0.2 wt. % of any other oxides; and
   (b) working the unfinished piece to form a dental prosthesis by means of a rotating tool having a circumference and being made of metal-bonded diamond grains with speeds of revolution for the tool of 10,000 to 50,000 revolutions per minute, with a first movement of the tool towards the piece of 0.1 to 0.5 millimeters per minute, and a second movement of the tool perpendicular to the first movement of 0.3 to 3.0 centimeters per second, and rotational speed along the circumference of the tool of 0.5 to 9.0 m/sec.

2. A process in accordance with claim 1, wherein the unfinished piece is densely vitrified.

3. A process in accordance with claim 1, wherein the unfinished piece is correspondingly preshaped in the porous condition of the dental prosthesis and then is densely vitrified.

4. A process in accordance with claim 1, wherein said unfinished piece is infiltrated.

5. A process in accordance with claim 1, wherein the unfinished piece is made as an unfinished prosthesis by slip casting, then drying, baking, redensifying hot-isostatically, and then treating by oxidizing.

6. A process in accordance with claim 1, wherein the working is carried out by means of digital acquisition and calculation of the mass of a prosthesis model, inputting the acquisition and calculation data into a data-processing control unit, and outputting the data to a processing device movable in three dimensions in order to move the piece.

7. A process in accordance with claim 1, wherein the unfinished piece is made out of yttrium stabilized, predominantly tetragonally shaped zirconium oxide.

* * * * *